United States Patent
Byron et al.

(10) Patent No.: US 10,426,410 B2
(45) Date of Patent: Oct. 1, 2019

(54) SYSTEM AND METHOD TO TRAIN SYSTEM TO ALLEVIATE PAIN

(71) Applicant: International Business Machines Corporation, Armonk, NY (US)

(72) Inventors: Donna K. Byron, Petersham, MA (US); Jana H. Jenkins, Raleigh, NC (US); Florian Pinel, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/824,484

(22) Filed: Nov. 28, 2017

(65) Prior Publication Data

US 2019/0159736 A1     May 30, 2019

(51) Int. Cl.
| | | |
|---|---|---|
| *A61B 5/00* | (2006.01) | |
| *A61M 21/00* | (2006.01) | |
| *G06F 3/16* | (2006.01) | |
| *G16H 40/60* | (2018.01) | |
| *A61M 21/02* | (2006.01) | |

(Continued)

(52) U.S. Cl.
CPC .......... *A61B 5/7267* (2013.01); *A61B 5/4848* (2013.01); *A61M 21/00* (2013.01); *A61M 21/02* (2013.01); *G06F 3/165* (2013.01); *G16H 40/60* (2018.01); *H04H 60/33* (2013.01); *H04H 60/61* (2013.01); *A61H 2230/00* (2013.01);

(Continued)

(58) Field of Classification Search
CPC .............. G06F 3/165; G06F 17/30772; G06F 17/30766; G06F 17/30749; G06F 17/30761; G06F 17/30752; H04H 60/06; H04H 60/07; H04H 60/33; H04H 60/35; H04H 60/45; H04H 60/46; H04H 60/61; H04H 60/65; H04H 60/66; H04H 60/68; H04H 60/73; A61M 21/02; A61M 2021/0027; A61B 5/72; A61B 5/7267; A61B 5/4848; A61B 5/4884; A61H 2230/00
USPC ................................................ 700/94; 600/28
See application file for complete search history.

(56) References Cited

U.S. PATENT DOCUMENTS

| | | | |
|---|---|---|---|
| 6,048,310 A | * | 4/2000 | Yasushi ............... A61B 5/02 600/300 |
| 6,364,842 B1 | | 4/2002 | Amano et al. |

(Continued)

OTHER PUBLICATIONS

Grace Chu-Hui-Lin Chi et al., Selection of Music for Inducing Relaxation and Alleviating Pain, Holist Nurs Pract. May-Jun. 2011;25(3):127-35.

(Continued)

*Primary Examiner* — Jesse A Elbin
(74) *Attorney, Agent, or Firm* — Terrile, Cannatti & Chambers, LLP; Stephen A. Terrile

(57) ABSTRACT

A method, system and computer-usable medium for training an information processing system to utilize personalized audio selection to facilitate achieving a target state comprising: identifying target states for a plurality of users; identifying a type of user for each of the plurality of users; identifying a plurality of sets of audio selections for each of the plurality of users; monitoring reactions by each of the plurality of users to each of the plurality of sets of audio selections; and, associating a set of audio selections from the plurality of sets of audio selections with a type of a user based upon the reactions by the plurality of users to the set of audio selections.

17 Claims, 4 Drawing Sheets

(51) Int. Cl.
*H04H 60/33* (2008.01)
*H04H 60/61* (2008.01)
*G06F 19/00* (2018.01)
*H04H 60/35* (2008.01)
*H04H 60/46* (2008.01)

(52) U.S. Cl.
CPC . *A61M 2021/0027* (2013.01); *G06F 19/3418* (2013.01); *H04H 60/35* (2013.01); *H04H 60/46* (2013.01)

(56) References Cited

U.S. PATENT DOCUMENTS

| | | |
|---|---|---|
| 6,484,062 B1 | 11/2002 | Kim |
| 7,396,990 B2 | 7/2008 | Lu et al. |
| 7,571,183 B2 | 8/2009 | Renshaw et al. |
| 8,306,981 B2 | 11/2012 | Westerink et al. |
| 8,583,615 B2 | 11/2013 | White et al. |
| 8,636,640 B2 | 1/2014 | Chang |
| 2004/0237759 A1 | 12/2004 | Bill |
| 2005/0131273 A1 | 6/2005 | Asano et al. |
| 2006/0054007 A1 | 3/2006 | Lu et al. |
| 2006/0235753 A1 | 10/2006 | Kameyama |
| 2009/0069914 A1 | 3/2009 | Kemp et al. |
| 2009/0216629 A1 | 8/2009 | James |
| 2010/0191037 A1 | 7/2010 | Cohen |
| 2010/0312042 A1 | 12/2010 | Anderson et al. |
| 2011/0160550 A1 | 6/2011 | Hwang et al. |
| 2011/0260830 A1 | 10/2011 | Weising |
| 2012/0323090 A1 | 12/2012 | Bechtel et al. |
| 2013/0232482 A1* | 9/2013 | Hassan ............... G06F 8/71 717/178 |
| 2016/0021425 A1* | 1/2016 | Eriksson ............ H04H 60/46 725/10 |

OTHER PUBLICATIONS

List of IBM Patents or Applications Treated as Related, 2018.

Mary Bates, BrainFacts.org, Senses and Perception, A Dose of Music for Pain Relief, Jan. 30, 2013, http://www.brainfacts.org/sensing-thinking-behaving/senses-and-perception/articles/2013/a-dose-of-music-for-pain-relief/.

Jae-Woo Chung et al., The Affective Remixer: Personalized Music Arranging, Conference on Human Factors in Computing Systems—Proceedings, Dec. 1, 2006, pp. 393-398, https://www.media.mit.edu/speech/papers/2006/AffectRemix-FINAL.pdf.

* cited by examiner

SYSTEM AND METHOD TO TRAIN SYSTEM TO ALLEVIATE PAIN

BACKGROUND OF THE INVENTION

Field of the Invention

The present invention relates in general to the field of computers and similar technologies, and in particular to software utilized in this field. Still more particularly, it relates to a method, system and computer-usable medium for training a system to alleviate pain.

Description of the Related Art

Many suffer pain. Some have chronic problems and others have injuries or conditions that plague them over time.

SUMMARY OF THE INVENTION

A method, system and computer-usable medium are disclosed for training an information processing system to utilize personalized audio selection to facilitate achieving a target state comprising: identifying target states for a plurality of users; identifying a type of user for each of the plurality of users; identifying a plurality of sets of audio selections for each of the plurality of users; monitoring reactions by each of the plurality of users to each of the plurality of sets of audio selections; and, associating a set of audio selections from the plurality of sets of audio selections with a type of a user based upon the reactions by the plurality of users to the set of audio selections.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

DETAILED DESCRIPTION

Various aspects of the present disclosure include an appreciation that certain music, some of which may be considered pleasant by the listener, can help alleviate pain. More specifically, brain scans reveal that listening to certain types of music increases activity in parts of the reward center of the brain. Pleasant music triggers the release of the brain chemical dopamine. The release of dopamine is strongly associated with other rewarding and motivating stimuli, such as food, sex, and certain addictive drugs. It is believed that the use of music to cause a change to a patient's mood may be a way to help to alleviate pain.

Figure 1:
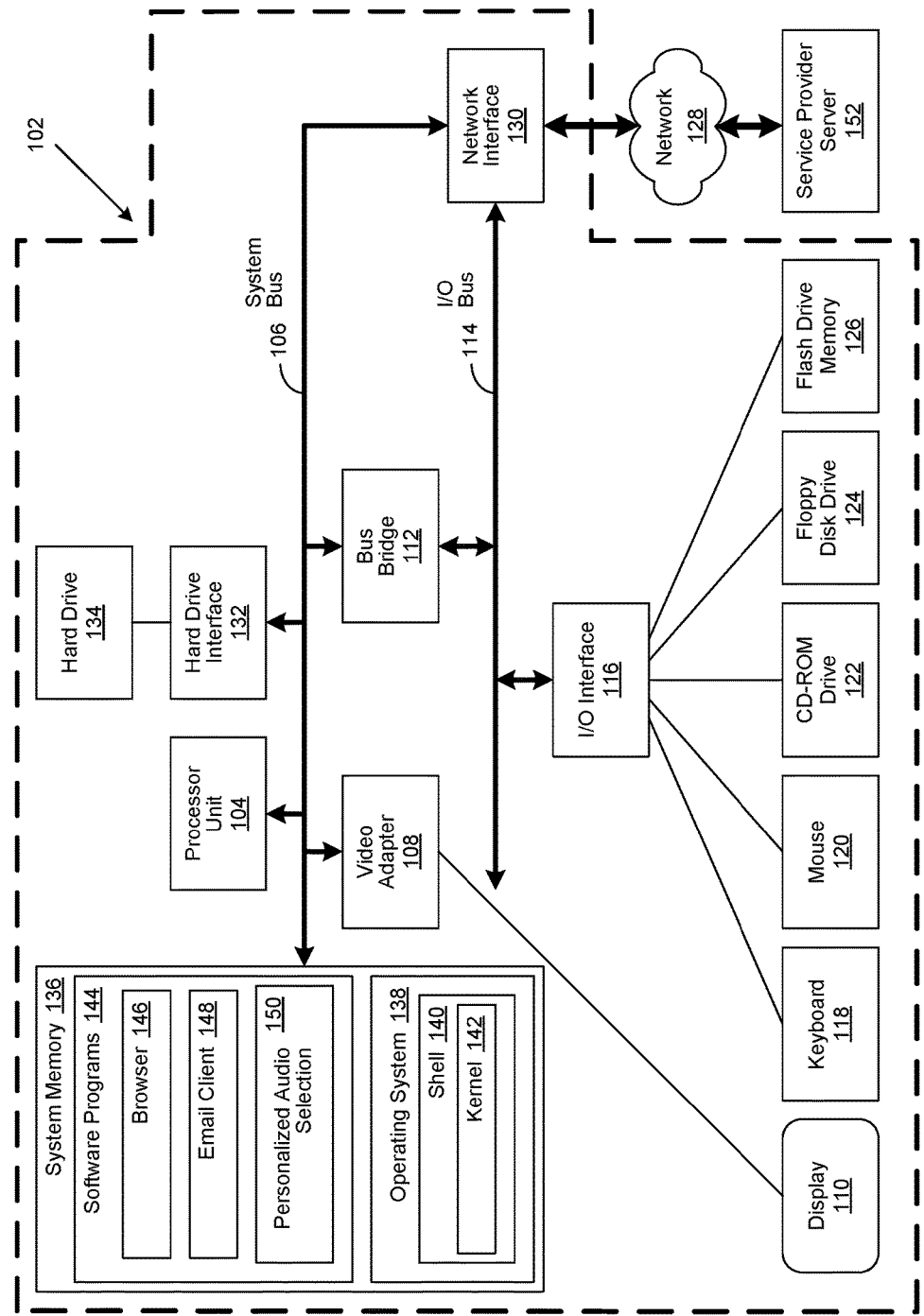
FIG. 1 depicts an exemplary client computer in which the present invention may be implemented.

FIG. 1 is a block diagram of an exemplary computer system 102 in which the present invention may be utilized or implemented. Computer system 102 includes a processor unit 104 that is coupled to a system bus 106. A video adapter 108, which controls a display 110, is also coupled to system bus 106. System bus 106 is coupled via a bus bridge 112 to an Input/Output (I/O) bus 114. An I/O interface 116 is coupled to I/O bus 114. The I/O interface 116 affords communication with various I/O devices, including a keyboard 118, a mouse 120, a Compact Disk—Read Only Memory (CD-ROM) drive 122, a floppy disk drive 124, and a flash drive memory 126. The format of the ports connected to I/O interface 116 may be any known to those skilled in the art of computer architecture, including but not limited to Universal Serial Bus (USB) ports.

Computer system 102 is able to communicate with a service provider server 152 via a network 128 using a network interface 130, which is coupled to system bus 106. Network 128 may be an external network such as the Internet, or an internal network such as an Ethernet Network or a Virtual Private Network (VPN). Using network 128, computer system 102 is able to use the present invention to access service provider server 152.

A hard drive interface 132 is also coupled to system bus 106. Hard drive interface 132 interfaces with a hard drive 134. In a preferred embodiment, hard drive 134 populates a system memory 136, which is also coupled to system bus 106. Data that populates system memory 136 includes the client computer's 102 operating system (OS) 138 and software programs 144.

OS 138 includes a shell 140 for providing transparent user access to resources such as software programs 144. Generally, shell 140 is a program that provides an interpreter and an interface between the user and the operating system. More specifically, shell 140 executes commands that are entered into a command line user interface or from a file. Thus, shell 140 (as it is called in UNIX®), also called a command processor in Windows®, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. While shell 140 generally is a text-based, line-oriented user interface, the present invention can also support other user interface modes, such as graphical, voice, gestural, etc.

As depicted, OS 138 also includes kernel 142, which includes lower levels of functionality for OS 138, including essential services required by other parts of OS 138 and software programs 144, including memory management, process and task management, disk management, and mouse and keyboard management. Software programs 144 may include a browser 146 and email client 148. Browser 146 includes program modules and instructions enabling a World Wide Web (WWW) client (i.e., computer system 102) to send and receive network messages to the Internet using HyperText Transfer Protocol (HTTP) messaging, thus enabling communication with service provider server 152. In various embodiments, software programs 144 may also include a cross platform reward exchange system 150. In these and other embodiments, the personalized audio selection system 150 includes code for implementing the processes described hereinbelow. In one embodiment, computer system 102 is able to download the personalized audio selection system 150 from a service provider server 152.

The hardware elements depicted in computer system 102 are not intended to be exhaustive, but rather are representative to highlight components used by the present invention. For instance, computer system 102 may include alternate memory storage devices such as magnetic cassettes, Digital Versatile Disks (DVDs), Bernoulli cartridges, and the like. These and other variations are intended to be within the spirit, scope and intent of the present invention.

Figure 2:
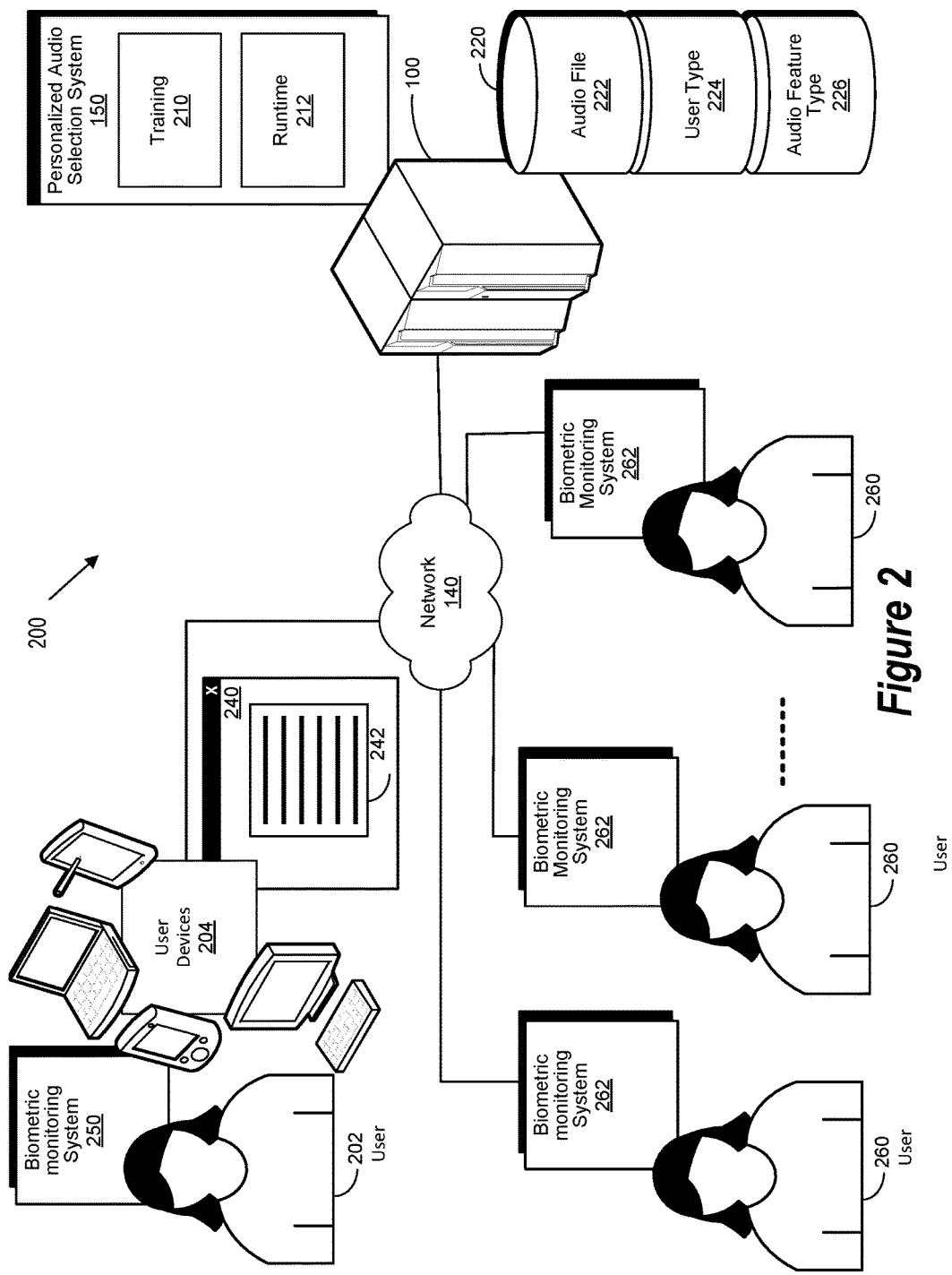
FIG. 2 shows a block diagram of a personalized audio selection environment.

FIG. 2 is a block diagram of a personalized audio selection environment 200 implemented in accordance with an embodiment of the invention. The personalized audio selection environment 200 includes a personalized audio selection system 150.

In general, the personalized audio selection operation includes a personalized audio selection training operation and a runtime personalized audio selection operation. During the personalized audio selection training operation, an audio piece is generated under control of an information processing system and states of a plurality of people (P1, P2-Pk) (e.g., patients) are measured while listening to various musical or other audio pieces. The states of the patients along with the audio piece that is associated with the state are stored within an information processing system. In various embodiments, the state of the patient is based upon a dopamine level of the patient or a stress level of a patient. During the personalized audio selection training operation, a personalized audio selection system 150 develops a plurality of models (M1, M2, -Mn) to predict an impact of a particular audio piece on users belonging to a particular group.

During the personalized audio selection runtime operation, models developed during the personalized audio selection training operation are used to create a playlist for a particular user. This playlist will cause a user to transition from a current state to a desired state. In certain embodiments, vital signs and other measures are monitored during the personalized audio selection runtime operation to determine the success of the particular audio files on the particular patient. In certain embodiments, the personalized audio selection runtime operation determines whether any subsequent adjustments and/or changes should be made to the playlist for the particular user. In certain embodiments, the information regarding subsequent adjustments and/or changes is provided to the personalized audio selection training operation.

Audio file selections are personalized to a patient or group of patients, as the same audio file does not necessarily have the same effect on everyone. In certain embodiments, the pain alleviation operation is adaptive and quickly modifies a suggested playlist via a continuous feedback loop.

In certain embodiments, the personalized audio selection operation provides pain relief for chronic disease care or end-of-life applications. Additionally, it will be appreciated that in certain embodiments, the personalized audio selection operation may be used to produce any desired physiological or emotional state.

In various embodiments, a user 202 interacts with the personalized audio selection system 150 to perform a personalized audio selection operation. In various embodiments, the personalized audio selection system 150 executes on a hardware processor of a computer system 102. In these and other embodiments, the user 202 may use a user device 204 to interact with the personalized audio selection system 150.

As used herein, a user device 204 refers to an information processing system such as a personal computer, a laptop computer, a tablet computer, a personal digital assistant (PDA), a smart phone, a mobile telephone, or other device that is capable of communicating and processing data. In various embodiments, the user device is configured to present a personalized audio selection user interface 240. In various embodiments, the user device 204 is used to exchange information between the user 202, one or more biometric monitoring systems 250 (such as one or more of an electro cardiogram (ECG) measurement device, a blood pressure monitor, a pulse oximeter, a thermometer, a vascular Doppler measurement device, and a dopamine monitoring device) and the personalized audio selection system 150 through the use of a network 140. In certain embodiments, spontaneous eye-blink rate measurement is used to provide a proxy for dopamine level. In various embodiments, the personalized audio selection system 150 exchanges information from one or more training users 262 via one or more respective biometric monitoring systems 262 (such as an electro cardiogram (ECG) measurement device, blood pressure measurement device, a pulse oximeter, a thermometer, a vascular Doppler measurement device, and dopamine monitoring device) and the personalized audio selection system 150 through the use of a network 140. In various embodiments, each biometric monitoring system 262 monitors biometric activity of a respective training user 260. In various embodiments, the biometric activity can include one or more of heart rate, blood pressure, temperature and blood flow. In various embodiments, the biometric activity can include spontaneous eye-blink rate. In certain embodiments, the network 140 may be a public network, such as the Internet, a physical private network, a wireless network, a virtual private network (VPN), or any combination thereof. Skilled practitioners of the art will recognize that many such embodiments are possible and the foregoing is not intended to limit the spirit, scope or intent of the invention.

In certain embodiments, the personalized audio selection system 150 includes one or more of a training module 210 which performs a personalized audio selection training operation and a runtime module 212 which performs a personalized audio selection runtime operation. In various embodiments, the personalized audio selection environment 200 includes a storage repository 220. The storage repository may be local to the system executing the personalized audio selection system 150 or may be executed remotely. In various embodiments, the storage repository includes one or more of an audio file repository 222, a user type repository 224 and an audio feature type repository 226.

In various embodiments, the user device 204 presents a personalized audio selection user interface 240. In various embodiments, the personalized audio selection user interface provides access to one or more personalized audio selection options 242. In various embodiments, the personalized audio selection options 242 allow a user to tailor audio selections provided by the personalized audio selection system 150 to further affect a biometric change in response to the audio selections. In various embodiments, a personalized audio selection user interface 240 may be presented via a website. In various embodiments, the website is provided by the personalized audio selection system 150. In various embodiments, the user 202 may interact with the personalized audio selection options 242 to control or receive information from the personalized audio selection system 150.

For the purposes of this disclosure a website may be defined as a collection of related web pages which are identified with a common domain name and is published on at least one web server. A website may be accessible via a public internet protocol (IP) network or a private local network. A web page is a document which is accessible via a browser which displays the web page via a display device of an information handling system. In various embodiments, the web page also includes the file which causes the document to be presented via the browser. In various embodiments, the web page may comprise a static web page which is delivered exactly as stored and a dynamic web page which is generated by a web application that is driven by software that enhances the web page via user input to a web server.

Figure 3:
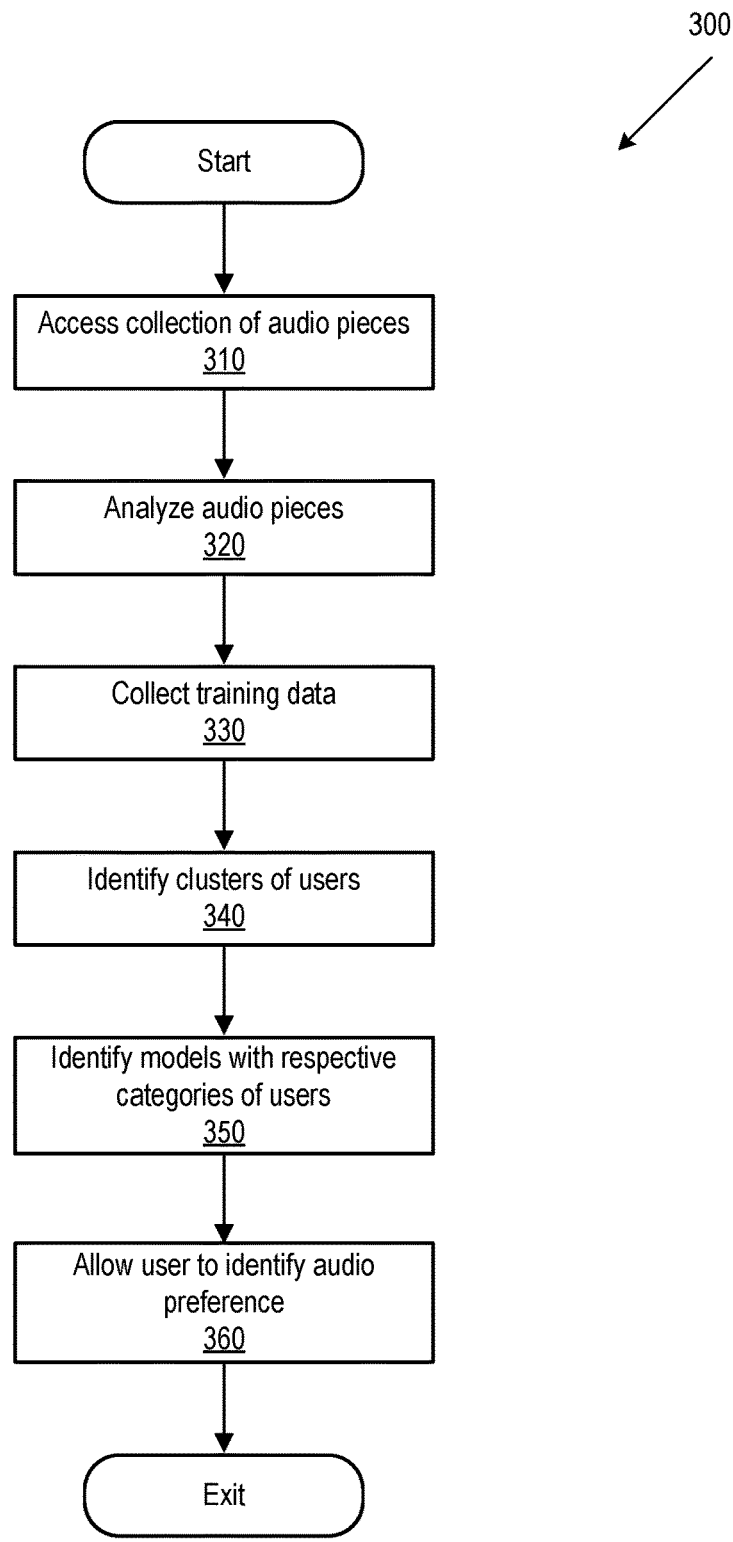
FIG. 3 shows a flow chart of a personalized audio selection training operation.

Referring to FIG. 3, a flow chart of a personalized audio selection training operation 300 is shown. More specifically, the personalized audio selection training operation 300 starts at step 310 with accessing a collection of audio pieces that could be either songs, musical constructions, white noise, nature recordings, etc. In certain embodiments, the collection of audio pieces is accessed from the audio repository 222. Next, at step 320 the personalized audio selection training operation 200 analyzes each piece of audio in the inventory and identifies feature vectors associated with each audio piece. In various embodiments, the feature vectors include one or more of tempo vectors, vectors representing a semantic analysis of lyrics (if any), style vectors, predominant instruments vectors, etc. For example, an audio piece with predominantly acoustic guitar might be more soothing than predominantly horn section music, depending on personal preferences. In various embodiments, the feature vectors could also include vectors representing intensity/energy level changes over the course of an audio piece. In certain embodiments, identifying feature vectors can include performing semantic analysis of lyrics using entity and entity relationship extraction. In certain embodiments, identifying feature vectors can include annotating style and instruments of a particular audio file. In certain embodiments, the annotating can include associating keywords with the audio piece (such as via metadata associated with the audio file). In certain embodiments, the feature vectors may be identified via an audio feature extraction tool such as the Yaafe audio feature extraction tool.

Next, at step 330, the personalized audio selection training module 210 collects training data regarding which features correlate to physiological/emotional state. When collecting training data, the personalized audio selection training module 210 observes physical characteristics of users (e.g., via the biometric monitoring systems 262) to learn models of which features of an audio file drive transitions from some source physiological user state to a desired physiological user state. In various embodiments, the physiological user states include a pain physiological user state, a pleasure physiological user state and a stress physiological user state. When collecting the training data, the personalized audio selection training module 210 either plays certain audio selections or modifies audio selections and observes the physiological user state to determine whether the audio selection achieve a desired change to a physiological state.

Next, at step 340, the personalized audio selection training module 210 identifies clusters of users who are affected by certain features. In certain embodiments, the clusters of users correspond to categories of users. Next at step 350, the personalized audio selection training module 210 identifies a plurality of models along with respective categories of users who are positively affected by a particular model. It will be appreciated that not everyone reacts to given features in the same way. Accordingly, the personalized audio selection training module 210 produces a plurality of models, each trained for a different category of users. In certain embodiments, the categories of users may include demographic categories, musical taste categories and audio stimuli reactive categories. In certain embodiments, the audio stimuli reactive categories may be derived from users of previous training sessions.

Next, at step 360, a user may identify a particular audio preference (e.g., musical preference) which can then be used in the training operation. For example, a specific user might prefer punk-rock as a destressing stimulus, while another prefers classical music. It will be appreciated that often particular users are not be consciously aware of which musical selections will actually reduce their physiological stress level. Accordingly, the training operation provides both observation-based clustering and grouping based on personal preferences.

Figure 4:
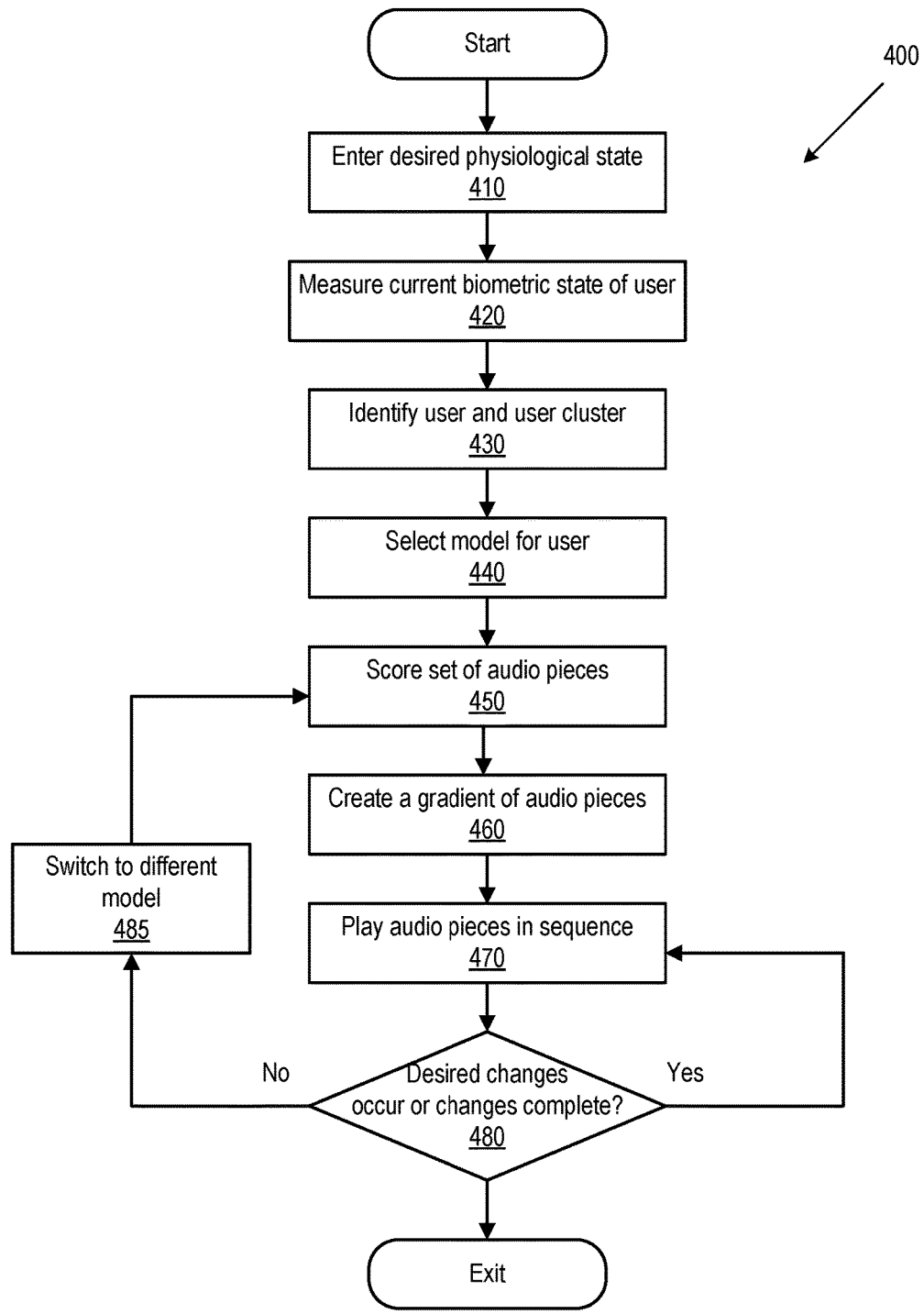
FIG. 4 shows a flow chart of a personalized audio selection runtime operation.

Referring to FIG. 4, a flow chart of a personalized audio selection runtime operation 400 is shown. In general, at runtime the personalized audio selection runtime module 212 iterates playing the audio and observing the patient for response for a particular patient. More specifically, the personalized audio selection runtime operation 400 starts at step 410 with a user or healthcare professional entering a desired physiological state via a personalized audio selection user interface 240. Next, at step 420, a biometric device measures a current state of the user. Next, at step 430, the personalized audio selection runtime module 212 identifies the user and a cluster associated with the user. Next, at step 440, the personalized audio selection runtime module 212 selects a best model for the user according to the desired physiological state and the cluster associated with the user. For returning users, the best model may be known by the personalized audio selection runtime module 212 from a previous session. For new users, the model can be selected based on their musical tastes or song playlists. For users who are unconscious or otherwise unable to provide information about their taste, the personalized audio selection runtime module 212 uses the most common model, as identified during the training phase.

Next, at step 450, once a model has been selected, a set of audio pieces (e.g., musical pieces or other sounds) is scored by the personalized audio selection runtime module 212 based upon the model. In certain embodiments the model can include a machine learning model. In certain embodiments, the machine learning model generates a numeric value (i.e., a score) that represents how likely a given audio selection is to induce a desired state transition or how well a given piece of audio is suited for a given mood, based on the audio's features. Next at step 460, a subset of the scored audio pieces are selected to create a gradient of the scored audio pieces, the gradient of scored audio pieces which will produce a change the current physiological state to the desired physiological state. In certain embodiments, the gradient is based on the scores. For example, to transition from a first mood (mood A) to a second mood (mood B), the subset of the scored audio pieces start with audio pieces that score equally for moods A and B and then slowly transition to pieces that score higher for mood B. The set of audio pieces can be an entire collection available to the healthcare professional, or the pieces that match the user's preferred genres, or a collection provided by the user. In certain embodiments, the starting point is an audio piece whose score (as evaluated by the model) is close to the current mood of the user. An additional scorer could be used to model the taste of the user.

Next at step 470 each audio piece is played in sequence to cause the desired physiological transitions. For example, the audio pieces might be normalized or might include a gradually stepped-down tempo, volume, etc. Next at step 480, the personalized audio selection runtime module 212 continues to monitor the physiological state of the user to detect whether the desired physiological changes are occurring. If the user is progressing toward their desired state, the personalized audio selection runtime module 212 continues playing the selected audio pieces. If the desired changes do not happen, then at step 485, the personalized audio selection runtime module 212 switches to a different model that better reflects the observed changes and control returns to step 450. In certain embodiments, the monitoring the physiological state of the user includes monitoring reactions by the user to the set of audio pieces to determine an assessment; and the switching to a different model includes adjusting the set of audio pieces responsive to determining when the assessment is below a desired level. The personalized audio selection module 212 can also determine whether to complete the personalized audio selection runtime operation at step 480

As will be appreciated by one skilled in the art, the present invention may be embodied as a method, system, or computer program product. Accordingly, embodiments of the invention may be implemented entirely in hardware, entirely in software (including firmware, resident software, microcode, etc.) or in an embodiment combining software and hardware. These various embodiments may all generally be referred to herein as a "circuit," "module," or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example, but not limited to, an electronic, magnetic, optical, electromagnetic, infrared, or semiconductor system, apparatus, or device. More specific examples (a non-exhaustive list) of the computer-readable medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, or a magnetic storage device. In the context of this document, a computer-usable or computer-readable medium may be any medium that can contain, store, communicate, or transport the program for use by or in connection with the instruction execution system, apparatus, or device.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Embodiments of the invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Although the present invention has been described in detail, it should be understood that various changes, substitutions and alterations can be made hereto without departing from the spirit and scope of the invention as defined by the appended claims.

What is claimed is:

1. A method for training an information processing system to utilize personalized audio selection to facilitate achieving a target state comprising:
   identifying target states for a plurality of users;
   identifying a type of user for each of the plurality of users;
   identifying a plurality of sets of audio selections for each of the plurality of users;
   monitoring reactions by each of the plurality of users to each of the plurality of sets of audio selections, the reactions by each of the plurality of users comprising biometric activity of each of the plurality of users, the reactions by each of the plurality of users being monitored via respective biometric monitoring systems;
   associating a set of audio selections from the plurality of sets of audio selections with a type of a user based upon the reactions by the plurality of users to the set of audio selections;
   monitoring reactions of a plurality of people P ($P_1$, $P_2$, ..., Pk) to audio selections A (Al, $A_2$, ..., Aj) to form a history of mappings;
   analyzing the history of mappings to form a plurality of models M ($M_1$, $M_2$, ..., Mn),
   each of the plurality of models predicting an impact of a particular audio piece on users belonging to a particular group, each of the plurality of models being trained for a different category of users; and
   providing a suggested model Mi for a user based on information about the user.

2. The method of claim 1, wherein:
   the information about the user is based on a plurality of factors, the plurality of factors comprising personal preferences, demography, and the target state of the user.

3. The method of claim 1, wherein:
   the target state is selected from a group of target states, the group of target states comprising a dopamine level, a stress level, a mood, a pulse rate.

4. The method of claim 1, further comprising:
audio selections from the plurality of audio selections are selected from a group of audio selections comprising songs, musical constructions, white noise, and nature recordings.

5. The method of claim 4, further comprising:
determining whether a gradient of audio selections affects the reactions of the users; and,
modifying the audio selections to provide the gradient of audio selections when the gradient of audio selections affects the reactions of the users.

6. A system comprising:
a processor;
a data bus coupled to the processor; and
a computer-usable medium embodying computer program code, the computer-usable medium being coupled to the data bus, the computer program code used for training an information processing system to utilize personalized audio selection to facilitate achieving a target state and comprising instructions executable by the processor and configured for:
identifying target states for a plurality of users;
identifying a type of user for each of the plurality of users;
identifying a plurality of sets of audio selections for each of the plurality of users;
monitoring reactions by each of the plurality of users to each of the plurality of sets of audio selections, the reactions by each of the plurality of users comprising biometric activity of each of the plurality of users, the reactions by each of the plurality of users being monitored via respective biometric monitoring systems;
associating a set of audio selections from the plurality of sets of audio selections with a type of a user based upon the reactions by the plurality of users to the set of audio selections;
monitoring reactions of a plurality of people P ($P_1$, $P_2$, ..., Pk) to audio selections A (Al, $A_2$, ..., Aj) to form a history of mappings;
analyzing the history of mappings to form a plurality of models M ($M_1$, $M_2$, ..., Mn), each of the plurality of models predicting an impact of a particular audio piece on users belonging to a particular group, each of the plurality of models being trained for a different category of users; and
providing a suggested model Mi for a user based on information about the user.

7. The system of claim 6, wherein:
the information about this user is based on a plurality of factors, the plurality of factors comprising personal preferences, demography, and the target state of the user.

8. The system of claim 6, wherein:
the target state is selected from a group of target states, the group of target states comprising a dopamine level, a stress level, a mood, a pulse rate.

9. The system of claim 6, wherein:
audio selections from the plurality of audio selections are selected from a group of audio selections comprising songs, musical constructions, white noise, and nature recordings.

10. The system of claim 9, wherein the instructions are further configured for:
determining whether a gradient of audio selections affects the reactions of the users; and,
modifying the audio selections to provide the gradient of audio selections when the gradient of audio selections affects the reactions of the users.

11. A non-transitory, computer-readable storage medium embodying computer program code, the computer program code comprising computer executable instructions configured for:
identifying target states for a plurality of users;
identifying a type of user for each of the plurality of users;
identifying a plurality of sets of audio selections for each of the plurality of users;
monitoring reactions by each of the plurality of users to each of the plurality of sets of audio selections, the reactions by each of the plurality of users comprising biometric activity of each of the plurality of users, the reactions by each of the plurality of users being monitored via respective biometric monitoring systems;
associating a set of audio selections from the plurality of sets of audio selections with a type of a user based upon the reactions by the plurality of users to the set of audio selections;
monitoring reactions of a plurality of people P ($P_1$, $P_2$, ..., Pk) to audio selections A (Al, $A_2$, ..., Aj) to form a history of mappings;
analyzing the history of mappings to form a plurality of models M ($M_1$, $M_2$, ..., Mn), each of the plurality of models predicting an impact of a particular audio piece on users belonging to a particular group, each of the plurality of models being trained for a different category of users; and
providing a suggested model Mi for a user based on information about the user.

12. The non-transitory, computer-readable storage medium of claim 11, wherein:
the information about the user is based on a plurality of factors, the plurality of factors comprising personal preferences, demography, and the target state of the user.

13. The non-transitory, computer-readable storage medium of claim 11, wherein:
the target state is selected from a group of target states, the group of target states comprising a dopamine level, a stress level, a mood, a pulse rate.

14. The non-transitory, computer-readable storage medium of claim 11, wherein:
audio selections from the plurality of audio selections are selected from a group of audio selections comprising songs, musical constructions, white noise, and nature recordings.

15. The non-transitory, computer-readable storage medium of claim 14, wherein the instructions are further configured for:
determining whether a gradient of audio selections affects the reactions of the users; and,
modifying the audio selections to provide the gradient of audio selections when the gradient of audio selections affects the reactions of the users.

16. The non-transitory, computer-readable storage medium of claim 11, wherein the computer executable instructions are deployable to a client system from a server system at a remote location.

17. The non-transitory, computer-readable storage medium of claim 11, wherein the computer executable instructions are provided by a service provider to a user on an on-demand basis.

* * * * *